United States Patent [19]

Bahrmann et al.

[11] Patent Number: 4,740,626

[45] Date of Patent: Apr. 26, 1988

[54] PROCESS FOR THE PREPARATION OF ALDEHYDES

[75] Inventors: Helmut Bahrmann, Hamminkeln; Werner Konkol; Jügen Weber, both of Oberhausen; Hanswilhelm Bach, Duisburg; Ludger Bexten, Hünxe, all of Fed. Rep. of Germany

[73] Assignee: Ruhrchemie Aktiengesellschaft, Oberhausen, Fed. Rep. of Germany

[21] Appl. No.: 907,033

[22] Filed: Sep. 12, 1986

[30] Foreign Application Priority Data

Sep. 26, 1985 [DE] Fed. Rep. of Germany ....... 3534314

[51] Int. Cl.⁴ ............................................. C07C 45/50
[52] U.S. Cl. .................................... 568/454; 568/455
[58] Field of Search ................................ 568/454, 455

[56] References Cited

U.S. PATENT DOCUMENTS

| | | | |
|---|---|---|---|
| 4,248,802 | 2/1981 | Kuntz | 568/454 |
| 4,399,312 | 9/1983 | Russell et al. | 568/454 |
| 4,487,972 | 12/1984 | Haag et al. | 568/454 |
| 4,510,332 | 4/1985 | Matsumoto | 568/454 |
| 4,578,523 | 3/1986 | Bahrmann et al. | 568/454 |
| 4,593,126 | 6/1986 | Cornils et al. | 568/454 |

*Primary Examiner*—Werren B. Lone
*Attorney, Agent, or Firm*—Jordan B. Bierman

[57] ABSTRACT

The present invention relates to a process for the preparation of aldehydes by the reaction of olefinic compounds with hydrogen and carbon monoxide in the presence of a catalyst system containing rhodium and aromatic phosphines. The aromatic phosphines are soluble in organic media and represent salts of sulfonated or carboxylated triarylphosphines which are insoluble in water. After hydroformylation, the reaction product is treated with a diluted aqueous solution of a base and the aqueous phase containing rhodium and aromatic phosphines is separated. Thus, thermal loading of the catalyst, for example by the redistillation of the reaction product, is avoided.

16 Claims, No Drawings

PROCESS FOR THE PREPARATION OF ALDEHYDES

This Application claims the priority of German P 35 34 314.1, filed September 26, 1985.

The present invention relates to a process for the preparation of aldehydes by the reaction of olefinic compounds with hydrogen and carbon monoxide at elevated temperatures and pressures. The reaction takes place in the homogeneous phase in the presence of a catalyst system containing rhodium and aromatic phosphines in molar excess. The catalyst is then separated from the reaction product.

The preparation of aldehydes and alcohols by the reaction of olefins with carbon monoxide and hydrogen is known. The reaction is catalyzed by hydridometalcarbonyls, preferably those of Group VIII of the Periodic Table. Apart from cobalt, which finds widespread commercial application as a catalyst metal, rhodium has been gaining significance in the past few years. In contrast to cobalt, rhodium permits the reaction to be carried out at low pressure; moreover, primarily straight-chain n-aldehydes and only a minor amount of iso-aldehydes are formed. Finally, with the use of rhodium catalysts, the hydrogenation of olefins to saturated hydrocarbons is also much lower than with the use of cobalt catalysts.

With the commercially established processes, the rhodium catalyst is used in the form of modified hydrido-rhodium carbonyls which contain additional and, in some cases, excess ligands. Tertiary phosphines or phosphites have proved particularly useful as ligands. Their application makes it possible to reduce the reaction pressure to under 30 MPa.

However, with this process the separation of the reaction products and the recovery of the catalysts homogeneously dissolved in the reaction product causes problems. Generally, the reaction product is distilled out of the reaction mixture. In practice, however, this route can only be employed for the hydroformylation of lower olefins; i.e. olefins with up to 5 carbon atoms in the molecule, owing to the thermal sensitivity of the aldehydes and alcohols formed.

When long-chain olefins or olefinic compounds with functional groups are hydroformylated, products with a high boiling point are formed which cannot be separated by distillation from the homogeneously dissolved rhodium complex catalyst. The thermal loading of the distillate leads, through the formation of heavy oil, to considerable losses of valuable products and catalysts through the decomposition of rhodium complexes.

The thermal separation of the catalyst is avoided by the use of water-soluble catalyst systems. Such catalysts are described, for example, in the DE-PS No. 26 27 354. Solubililty of the rhodium complex compounds is achieved by the use of sulfonated triarylphosphines as complex components. With this process variant, the catalyst is separated from the reaction product after completion of the hydroformylation reaction simply by separation of the aqueous and organic phases; i.e. without distillation and therefore without any additional thermal process steps. Another feature of this method is that n-aldehydes are formed with higher selectivity from terminal olefins, and iso-aldehydes are produced only to a very minor extent. Apart from sulfonated triarylphosphines, carboxylated triarylphosphines are also used as complex components of water-soluble rhodium complex compounds.

The use of water-soluble catalysts for the hydroformylation of lower olefins, in particular ethylene and propylene, has stood the test well. If higher olefins such as hexene, octene or decene are used, the conversion and/or selectivity of the reaction to n-compounds shows a marked decline. Often, the reaction is no longer economic for commercial scale preparation.

The problem, therefore, consisted in developing a process which permits the hydroformylation of olefinic compounds whose hydroformylation products exhibit a relatively high boiling point or are not distillable, followed by separation of the catalysts under the mildest possible conditions. This problem is solved by a process for the preparation of aldehydes by the reaction of olefinic compounds with hydrogen and carbon monoxide at 100° to 170° C. and 0.3 to 45 MPa in a homogeneous phase and in the presence of a catalyst system containing rhodium and aromatic phosphines in molar excess. Therefore, separation of the catalyst, which constitutes salts of sulfonated or carboxylated triarylphosphines which are soluble in organic media but insoluble in water, is effected by treating the hydroformylation product with a dilute aqueous solution of a base; the aqueous phase containing the catalyst system thereby separates.

The process according to the invention combines the advantages of the known hydroformylation processes without their disadvantages. On the one hand, it permits the hydroformylation of olefinic compounds in the homogeneous phase thus ensuring a high conversion. On the other hand, it permits a mild and near complete separation of the catalyst before any further processing of the reaction product by distillation, hydrogenation, or oxidation.

Suitable olefinic compounds are compounds with 6 to 20 carbon atoms having one or more olefinic bonds. They can be aliphatic, cycloaliphatic or araliphatic. Examples of aliphatic compounds are straight-chain and/or branched olefins with terminal and/or central positioning of the double bond. Straight-chain olefins with 6 to 12 carbon atoms are particularly suitable; e.g. n-hexene-1, n-heptene-1, n-octene-1, n-nonene-1, n-decene-1, n-undecene-1 and n-dodecene-1; also acyclic terpenes and branched olefins such as diisobutylene, tripropylene, tetrapropylene and dimersol, are suitable.

Examples of aliphatic dienes are 1,3-butadiene, 1,5-hexadiene and 1,9-decadiene. Examples of cycloaliphatic feed materials are cyclohexene, cyclooctene, dicyclooctadiene, dicyclopentadiene and cyclic terpenes such as limonene, pinene, camphorene and bisabolene. An example of araliphatic olefins is styrene.

The following deserve particular mention as olefinic compounds with functional groups: acrylic acid derivatives, in particular, the esters; allyl compounds, in particular the alcohols and esters; vinyl compounds, in particular the esters and ethers; cyanocompounds, in particular acrylonitrile, as well as acrolein derivatives.

Also useful are secondary amines ($NHR_2$) which contain a total of 10 to 40, in particular 12 to 34, and preferably 14 to 26, carbon atoms. Di-2-ethylhexylamine, diisooctylamine, diisononylamine and dicyclohexylamine are particularly effective. Operable tertiary amines ($NR_3$) have a total of 15 to 50, in particular 18 to 42, and preferably 21 to 39, carbon atoms. Triisooctylamine, tri-n-octylamine, triisononylamine, triisodecylamine, and triisotridecylamine are particularly suitable.

The catalyst system consists of salts of sulfonated or carboxylated triarylphosphines, which are soluble in organic media but insoluble in water, as well as rhodium, which is bound as a complex to the phosphorus atom. The cations of the salts contain the grouping $(NR_2H_2)^+$ and/or $(NR_3H)^+$, wherein R denotes alkyl groups with 4 to 12 carbon atoms, or aryl or cycloalkyl groups with 4 to 12 carbon atoms.

The cations of the following amines are particularly suitable: dicyclohexylamine (boiling point 256° C.), di-2-ethylhexylamine (boiling point 281° C.), triisooctylamine (boiling point 340° C.), tri-n-octylamine (boiling point 360° C.), triisononylamine (boiling point 345° C.), and triisodecylamine (boiling point 360° C.).

The olefinic compounds are hydroformylated at 100° to 170° C. and 0.3 to 45 MPa (3.0 to 450 bar) in the presence of 5 to 500 ppm rhodium, preferably 10 to 150 ppm rhodium based on the olefinic compound. The salts of the sulfonated or carboxylated triarylphosphines are employed in a ratio of 5:1 to 200:1, preferably 10:1 to 100:1 (mols triarylphosphine salt per g-atom rhodium). The olefinic compound can be introduced into the hydroformylation reaction either as such or in solution. Suitable solvents are, for example, cyclohexane, methylcyclohexane, toluene, and xylene.

The reaction conditions depend on the type of olefinic compound. For example, reactive feed materials can be reacted in the presence of very small amounts of catalyst at relatively low temperatures and pressures, whereas inactive substances require stronger conditions. Examples of reactive olefins are 1-hexene, 1-octene, 1-decene, 1-dodecene, cyclohexene, styrene. Examples of inactive olefins are 4-n-octene, tripropylene, tetrapropylene, dicyclopentadiene, limonene.

The synthesis gas employed customarily has the molar composition $CO:H_2=1:1$. However, it is also possible to deviate from this ratio. Generally, a $CO:H_2$ mixture of 5:1 to 1:5 is employed. Mono, di or trisulfonated triphenylphosphines namely $(C_6H_5)_2PC_6H_4SO_3H$, $C_6H_5P(C_6H_5SO_3H)_2$ or $P(C_6H_4SO_3H)_3$ have proved to be particularly useful sulfonated triarylphosphines. However, mixtures of mono, di and trisulfonated triphenylphosphines are also suitable as catalyst components.

After the hydroformylation, the reaction mixture is treated with a dilute aqueous solution of a water-soluble base. The water-soluble bases required for splitting the salts of sulfonated or carboxylated triarylphosphines which are soluble in organic media and insoluble in water must be sufficiently alkaline to produce the desired pH value during extraction of the hydroformylation mixture with a diluted solution of the base. The alkali or alkaline earth hydroxides fulfil this requirement, but aqueous tetraalkylammonium hydroxide solutions can also be used. The concentration of the water-soluble base is 0.05% by weight to 10% by weight, in particular 1 to 3% by weight, based on the aqueous solution.

By mixing of the two phases at temperatures of $\leq 70°$ C., preferably $\leq 40°$ C., the corresponding secondary or tertiary amines are liberated from the $(NR_2H_2)^+$ and $(NR_2H)^+$ salts and, at the same time, a water-soluble salt of the sulfonated or carboxylated triarylphosphine is formed. The latter enters the aqueous phase by extraction and is separated together with the rhodium which is complexed to the phosphorus atom. During this extraction the pH value of the mixture of the two phases should be $\geq 8$, preferably $\geq 8.5$. Generally, it is advisable to maintain a pH value of 8 to 13.7, preferably 8.5 to 10.5.

The extraction is simple to carry out. As a result of the reduced thermal loading, both deactivation and thermal decomposition are decreased and therefore the damage to the catalyst system is minimized. Furthermore, the formation of undesirable by-products formed from the hydroformylation product is also reduced. The recovery rate is already high in the first extraction and is over 70% by weight based on the rhodium employed. This result can be further improved by multiple extraction.

The organic and the aqueous phases separate quickly and completely from each other. In order to accelerate the separation of the two phases, a centrifuge can be employed, if necessary, and the top organic phase can then be separated from the bottom aqueous phase. Separators with coalescing elements have proved particularly successful.

The presence of air or oxygen is to be avoided as far as possible in order to prevent oxidation of the dissolved phosphine. If the trivalent phosphorus atom is oxidized, less rhodium is recovered during extraction. In such a case, it has been found useful to add fresh triarylphosphine to the material before extraction. After separation of the aqueous phase containing rhodium and triarylphosphine, the hydroformylation product is washed—if necessary—several times with cold water in order to remove any alkaline substances still present. This must be performed carefully in order to avoid alkali-catalyzed secondary reactions—e.g. aldolization—during hydrogenation.

Another advantage of the process according to the invention consists in the fact that the active hydroformylation catalyst can be recovered from the aqueous phase containing the rhodium without any complicated procedures. The extract is acidified, e.g. with mineral acids, until a pH of about 1 is attained; the aqueous phase is then further extracted with a secondary or tertiary amine dissolved in an organic solvent (e.g. benzene or toluene). In this manner, the amine salt of the sulfonated or carboxylated triarylphosphine which was originally employed is reformed. As it is not soluble in water, it passes over into the organic phase together with the complexed rhodium. The re-extract thus obtained can be re-employed directly as a hydroformylation catalyst. If necessary, the rhodium and/or the phosphorus (III) ligands can be topped up. The process can also be performed as a continuous operation.

In the following examples, the invention is illustrated in more detail:

Experiment 1

Preparation of the triisooctylammonium salt from TPPTS.

The sulfonation of triphenylphosphine with oleum and the subsequent further processing is described in DE-OS No. 32 35 030.

Based on this procedure, triphenylphosphine is reacted with oleum at room temperature and the mixture formed is hydrolyzed by the addition of cold water. Then a solution of triisooctylamine in toluene is added and the mixture is stirred for about 30 minutes. After stirring has been completed, the lower aqueous phase containing sulphuric acid is separated. After adjusting the pH to 4.6 by the addition of 3% aqueous sodium hydroxide, the aqueous phase separated and was disposed of. Then the toluene solution was washed two more times with water. This treatment took place in the complete absence of oxygen in order to avoid undesirable oxidation of the phosphine. In this manner, two phosphine mixtures I and II are prepared, the analytical data of which are listed in Table 1.

The following abbreviations are used herein:
TPPDS: triphenylphosphinedisulfonic acid salt
TPPTS: triphenylphosphinetrisulfonic acid salt
TPPODS: triphenylphosphine oxide disulfonic acid salt
TPPOTS: triphenylphosphine oxide trisulfonic acid salt
TPPSTS: triphenylphosphine sulfide trisulfonic acid salt
HPLC: high-pressure liquid chromatography

TABLE 1

(Values determined as sodium salts by means of the HPLC analysis)

|  | phosphine[1] mixture I | phosphine[1] mixture II |
|---|---|---|
| TPPDS | 1.714 weight-% | 0.677 weight-% |
| TPPTS | 8.087 weight-% | 2.80 weight-% |
| TPPODS | 0.205 weight-% | 0.108 weight-% |
| TPPOTS | 0.809 weight-% | 0.894 weight-% |
| P(III)[2] | 0.165 mol/kg | 0.075 mol/kg |

[1]amine salt solution in toluene
[2]determined iodometrically

EXAMPLE 1

In the following the hydroformylation of olefinic compounds is described.

An autoclave of suitable size equipped with a stirrer, a thermometer, and an inlet tube for the supply of synthesis gas, is rinsed with synthesis gas or nitrogen. Thereafter, the olefinic compound, the salt of the sulfonated triarylphosphine (prepared as described under Experiment 1), rhodium (in the form of rhodium-2ethylhexanoate) and, if necessary, a solvent, are introduced. The contents of the autoclave are pressurized by the introduction of synthesis gas ($CO:H_2 = 1:1$) and heated while stirring. The course of the reaction is monitored by the taking of samples during the reaction. The reaction conditions are given in the following Table 2.

TABLE 2

| Olefin: | Cyclohexane | Dimersol | Diisobutylene | Dicyclopentadiene | n-Hexene-1 | Limonene | n-Decene-1 |
|---|---|---|---|---|---|---|---|
| Amount of olefin (g) | 300 | 300 | 300 | 1000 | 2400 | 600 | 300 |
| Toluene (g) | 300 | 300 | 300 | — | — | 300 | 300 |
| Rhodium (related to olefin) | 10 ppm | 10 ppm | 30 ppm | 10 ppm | 10 ppm | 150 ppm | 50 ppm |
| TPPTS/TIOA* solution (g) | 18.7 | 18.7 | 17.8 | 187 | 150 | 561 | 93.5 |
| mmol P(III) | 3.1 | 3.1 | 2.9 | 30.9 | 24.8 | 92 | 15.4 |
| Rh:P(III) (molar) | 1:100 | 1:100 | 1:33 | 1:53.3 | 1:108 | 1:106 | 1:100 |
| Pressure (MPa) | 27 | 27 | 27 | 27 | 2,5 | 27 | 27 |
| Temperature °C | 130 | 130 | 130 | 130 | 130 | 130 | 130 |
| Reaction time (h) | 6 | 6 | 6 | 6 | 2,5 | 6 | 6 |
| Conversion (%) | 100 | 81 | 99 | 100 | 77 | 98 | 99 |
| Yield (%) | —** | 75 | 79 | —** | —** | 64 | 92 |

*Triphenylphosphine trisulfonate triisooctylamine dissolved in toluene
**not determined

EXAMPLE 2

Separation of the catalyst system containing the rhodium.

The reaction mixture from the hydroformylation is mixed with dilute aqueous alkali (3% NaOH by weight) with stirring and exclusion of air until the desired pH value has been attained. Then the stirring is discontinued and the mixture is left to separate. If necessary, the mixture of organic product and aqueous solution is centrifuged in order to accelerate the separation of the phases.

The majority of the rhodium-containing catalyst is in the aqueous phase in the form of the sodium salt of trisulfonated triarylphosphine. In order to gain more complete separation of the catalyst still present in the organic product, the extraction described above can be repeated one or several times, whereby the pH value is increased each time. Then the organic phase is washed thoroughly with water and, if necessary, with diluted acid in order to remove the last remains of the alkali.

The conditions of the extraction and the results obtained are given in the following Table 3.

TABLE 3

Separation of rhodium from the raw hydroformylation product

| Hydroformylated Olefin | Cyclohexane | Dimersol | Diisobutylene | Dicyclopentadiene | n-Hexene-1 | Limonene | n-Decene-1 |
|---|---|---|---|---|---|---|---|
| Amount | 426 g | 452 g | 458 g | 1164 g | 1038 g | 100 g | 533 g |
| Temperature | 10° C. | 6° C. | 6° C. | 6° C. | 10° C. | 10° C. | 10° C. |
| 1st Separation |  |  |  |  |  |  |  |
| pH value | 11.0 | 11.3 | 9.1 | 12.6 | 10.0 | 10.0 | 10.0 |
| Addition of 3% aqueous NaOH | 67.8 g | 47.6 g | 39.8 g | 165 g | 220 g | 340 g | 55 |
| Rhodium (% of the theoretical value) in aqueous phase | 29.0 | 28 (76.4)*[1] | 37.0 (61.7)*[1] | 55.7*[1] | 52.3 | 78.7*[1] | 65.9*[1] |
| 2nd separation |  |  |  |  |  |  |  |
| pH value | — | — | — | — | 13.1 | 13.7 | 13.0 |
| Addition of 3% aqueous NaOH | — | — | — | — | 47.3 | 23.5 | 18 |
| Water scrubbibg (amount of water added) | — | — | — | — | 300 g | 299 g | 190 g |
| Neutralisation*[2] | — | — | — | — | 15 g*[2] | 25,5*[2] | 3 g*[2] |

TABLE 3-continued

Separation of rhodium from the raw hydroformylation product

| Hydroformylated Olefin | Cyclohexane | Dimersol | Diisobutylene | Dicyclopentadiene | n-Hexene-1 | Limonene | n-Decane-1 |
|---|---|---|---|---|---|---|---|
| Rhodium (% of the theorectical value) in aqueous phases, total | 29 (76.4)[*1] | 28 (79.9)[*1] | 37 (65)[*1] | 69.5 | 67.2 | 82.3[*1] | 92(92)[*1] |

[*1] related to the rhodium determined in the hydroformylation product
( )[*1] related to the rhodium determined in the hydroformylation product
[*2] diluted $H_2SO_4$ (0.5%-1.5% in water)

EXAMPLE 3

Recovery of the rhodium-containing catalyst and transfer into its active form.

The aqueous extract is acidified with diluted acid (e.g. 1% $H_2SO_4$) until a pH value of about 1 to 2 is attained. The active catalyst is e-extracted with a solution of the relevant amine originally used, in an organic solvent. It is intensively mixed and the amine reacts with the acidic aqueous phase. The amine salt formed is insoluble in water and passes into the organic solvent. Thus the hydroformylation catalyst is present in its original form. Any losses of rhodium and/or phosphine ligand are made up by the addition of fresh rhodium and/or ligand.

When this worked-up catalyst is re-employed in the hydroformylation, almost the same results are achieved as are set forth in Tables 2 and 3.

What we claim is:

1. A process for the preparation of comprising reacting olefins with hydrogen and carbon monoxide in the presence of a catalyst system containing rhodium and water insoluble, organic solvent soluble salts of sulfonated or carboxylated triarylphosphines to form a homogeneous mixture, contacting said mixture with an aqueous solution of a base, whereby said mixture separates into an organic phase and an aqueous phase.

2. The process of claim 1 wherein said salts are present in molar excess.

3. The process of claim 1 wherein said solution is diluted.

4. The process of claim 1 wherein said reacting takes place at about 100° to about 170° C. and about 0.3 to 45 MPa.

5. The process of claim 1 wherein said salts contain $[NR_2H_2]+$ and/or $[NR_3H]+$ as cations, R being alkyl having 4 to 12 carbon atoms, or aryl or cycloalkyl having 6 to 12 carbon atoms.

6. The process of claim 1 wherein said catalyst system comprises 5 to 500 ppm rhodium, based on said olefin, and the molar ratio of said salts to said rhodium about 5:1 to about 200:1.

7. The process of claim 6 wherein said system comprises 10 to 150 ppm rhodium, based on said olefin, and said molar ratio is about 10:1 to about 100:1.

8. The process of claim 1 wherein sulfonated triarylphosphine is mono-, di-, or trisulfonated triphenylphosphine.

9. The process of claim 8 wherein said phosphine is a mixture of mono-, di-, and trisulfonated phosphines.

10. The process of claim 1 wherein said contacting takes place at a temperature $\leq 70°$ C. and a pH of $\geq 8$.

11. The process of claim 10 wherein said temperature is $\leq 40°$ C. and said pH is $\geq 8.5$.

12. The process of claim 1 wherein said base is an alkali hydroxide, alkaline earth hydroxide, or alkyl ammonium hydroxide.

13. The process of claim 1 further comprising applying centrifugal force to said homogeneous mixture to aid separation.

14. The process of claim 1 wherein coalescing agents are used to aid separation of said homogeneous mixture.

15. The process of claim 1 wherein said aqueous phase is acidified and contacted with an amine dissolved in a water insoluble organic solvent, said amine being of the formula $NHR_2$ or $NR_3$, wherein R is alkyl having 4 to 12 carbon atoms, or aryl or cycloalkyl having 6 to 12 carbon atoms, said organic phase, after separation, being recycled to said reaction.

16. The process of claim 1 wherein said olefins have 6 to 20 carbon atoms.

* * * * *